United States Patent [19]

Sandine et al.

[11] 4,382,965
[45] May 10, 1983

[54] METHOD AND STARTER COMPOSITIONS FOR THE GROWTH OF ACID PRODUCING BACTERIA AND BACTERIAL COMPOSITION PRODUCED THEREBY

[75] Inventors: William E. Sandine; James W. Ayres, both of Corvallis, Oreg.

[73] Assignee: State of Oregon, acting by and for the State Board of Higher Education on behalf of Oregon State University, Corvallis, Oreg.

[21] Appl. No.: 279,340

[22] Filed: Jul. 1, 1981

Related U.S. Application Data

[63] Continuation of Ser. No. 52,960, Jun. 28, 1979, Pat. No. 4,282,255.

[51] Int. Cl.³ .............. A23C 9/12; A23C 9/127; C12N 1/20
[52] U.S. Cl. .............................. 426/7; 426/34; 426/36; 426/42; 426/43; 435/139; 435/253
[58] Field of Search .................... 435/139–141, 435/144, 253; 426/7, 34, 36, 42, 43

[56] References Cited

U.S. PATENT DOCUMENTS

| | | | |
|---|---|---|---|
| 1,913,346 | 6/1933 | Stiles | 435/140 X |
| 2,549,765 | 4/1951 | Beesch et al. | 435/140 |
| 3,715,276 | 2/1973 | Takasaki et al. | 435/94 |
| 3,792,171 | 2/1974 | Little | 426/38 |
| 3,937,798 | 2/1976 | Kitajima et al. | 423/659 |
| 4,053,642 | 10/1977 | Hup et al. | 426/36 |

FOREIGN PATENT DOCUMENTS 651541 11/1937 Fed. Rep. of Germany .
1031371 3/1953 France .

OTHER PUBLICATIONS

Richardson, J., *Dairy and Ice Cream Field*, 161(9), 80A–80D (1978).

*Primary Examiner*—Lionel M. Shapiro
*Attorney, Agent, or Firm*—Klarquist, Sparkman, Campbell, Leigh, Whinston & Dellett

[57] ABSTRACT

A method for growing acid producing bacteria in the presence of an essentially water insoluble or a temporarily water insolubilized and thus initially solid form of a neutralizing agent in a growth medium is described. The water insoluble or insolubilized neutralizing agent is a base, basic salt or mixture thereof adapted to provide a controlled reaction with the acid produced by the bacteria without substantially raising the pH of the growth medium. Preferably the neutralizing agent is in a water insoluble form. Bulk starter compositions for growing the bacteria including the insoluble or the insolubilized neutralizing agent are also described. Further, bacterial compositions with enhanced storability and viability because of the insoluble or the insolubilized neutralizing agent are described. The method and bulk starter compositions are particularly adapted to growing lactic acid producing bacteria which are then used in making food and beverage products for animals and humans.

18 Claims, No Drawings

METHOD AND STARTER COMPOSITIONS FOR THE GROWTH OF ACID PRODUCING BACTERIA AND BACTERIAL COMPOSITION PRODUCED THEREBY

This application is a continuation of application Ser. No. 52,960, filed June 28, 1979, now U.S. Pat. No. 4,282,255.

BACKGROUND OF THE INVENTION

1. Field of the Invention

The present invention relates to a method and to bulk starter compositions for growing acid producing bacteria by using an essentially water insoluble or temporarily water insolubilized and thus initially solid form of a neutralizing agent in the growth medium which is adapted to provide a controlled reaction with the acid produced by the bacteria without substantially raising the pH of the growth medium. In particular, the present invention relates to a preferred method wherein the solid form of the neutralizing agent maintains a selected pH range in the growth medium by a controlled reaction of an insoluble form of the neutralizing agent over a period of time with the acid produced by the bacteria.

2. Prior Art

Encapsulating techniques and encapsulated products for the controlled release of materials as a function of the destruction of the encapsulating agent over a period of time are well known to the prior art. For instance, Gutcho, M. H. 1976, *Microcapsules and Microencapsulation Techniques.* Noyes Data Corp. Park Ridge, N.J. provides many examples of both.

In the field of microbiology, time-releasing capsules have been used to provide for the delayed controlled release of components of bacteriological media where identifying test reactions to the released components are required (Sveum, W. H. and P. A. Hartman, 1977, *Appl. and Environ. Microbiol.*, 33:630–634; Lanz. W. W. and P. H. Hartman, 1976 *Appl. and Environ. Microbiol,* 32:716–722). They also have been used for the delayed release of nutrients in growing mushrooms (Carroll, A. D. and L. C. Schisler, 1976, *Appl. and Environ. Microbiol.*, 31:499–593); for the delayed release of gluconic acid as an acidulating agent during the smoking of sausage (Rugala, W., 1978, *Food Engineering,* 50:174); and, for incorporating ripening agents into cheese (Magee, E., Jr. and N. F. Olson, 1978, *Proceedings* 73rd Annual Meeting Am. Dairy Sci. Assn., p. 114).

In prior art unrelated to microbiology, methods and compositions for controlling pH by use of encapsulated alkaline or acid releasing materials are described for instance in U.S. Pat. No. 3,937,798 and in related patents which include U.S. Pat. Nos. 2,845,354; 3,133,862; 3,242,051; 3,622,350; 3,639,306; 3,792,171; 3,943,063; 3,949,094; 3,949,096; 3,952,110; 3,959,499; 3,976,794; 3,985,913; 3,996,156 and 4,004,039. This is also described in Food Product Development Vol 10 No. 6 pages 19 and 20 (July–August 1976). These patents describe methods and materials which can be used in the present invention providing they are non-toxic to acid producing bacteria in the growth medium. The use of essentially water insoluble or temporarily water insolubilized neutralizing agents to control the pH in cultures of acid-producing bacteria has not been made by the prior art so far as is known.

It is well known to those skilled in the art that neutralization is very important to the growth of acid producing bacteria. The reason for this is that the acid produced impairs the bacteria and will eventually injure and kill them, especially at pH's of 5.0 and below. Thus it is a common practice to provide for continuous neutralization by the continuous addition of a water soluble base or basic aqueous solution such as sodium hydroxide, potassium hydroxide, ammonium hydroxide, or ammonia gas so as to provide a pH which is neutral or slightly acid. Specialized equipment has been developed to monitor the pH of the growth medium and to add the neutralizing agent as needed. One patent describing this method is U.S. Pat. No. 4,021,304.

The present state of the art in growing bacteria to high cell counts for use as bacterial starters in preparing fermented dairy products such as cheese has been detailed recently (Sandine, W. E., (1977), *J. Dairy Sci.,* 60:822–828; and Sandine, W. E., (1979), *Lactic Starter Culture Technology.* Pfizer, Inc. New York, N.Y.). Numerous cheese plants in the United States are installing gaseous ammonia injection systems and pH recording devices in order to neutralize injurious acid produced during the growth of the bacteria. These systems, which are costly and require technical training to operate and maintain, have been described in a number of publications particularly Richardson, G. H., *Dairy and Ice Cream Field* 161(9):80A–80D (1978).

SUMMARY OF THE INVENTION

Objects

It is therefore an object of the present invention to provide a method which uses essentially water insoluble or temporarily water insolubilized neutralizing agents during the growth of acid-producing bacteria so as to maintain a pH which minimizes the adverse effects of the acid and maximizes the number and fermentation activity of the cells. It is further an object of the present invention to provide a method and bulk starter compositions which are relatively inexpensive and simple to use and which eliminate the need for costly equipment for dispensing a water soluble neutralizing agent into a bacterial growth medium. Further still, it is an object of the present invention to provide novel compositions which are easily adapted to commercial fermentation processes and which do not require external pH control by the addition of a water soluble base or basic solution. In addition it is a particular object of the present invention to provide a method and bulk starter compositions which are adapted to growing lactic acid producing bacteria which can be held at ambient room temperatures for at least 24 hours. These and other objects will become increasingly apparent by reference to the following description.

GENERAL DESCRIPTION

The present invention relates to the improvement in a method for growing acid producing bacteria by inoculating the bacteria into a growth medium containing water and nutrients for the bacteria and then growing the bacteria in the growth medium which comprises: providing an essentially water insoluble or temporarily water insolubilized and thus initially solid form of a non-toxic neutralizing agent which is a base, basic salt or mixture thereof in the growth medium such that a portion of the neutralizing agent remains in solid form in the medium over a period of time; and growing the bacteria in the growth medium in the presence of the insoluble or the insolubilized neutralizing agent, wherein a pH range in the medium is maintained so as to promote growth of the bacteria by a controlled reaction of the insoluble or the insolubilized neutralizing agent with at least a part of the acid produced by the bacteria in the medium over the period of time.

The present invention also relates to a bulk starter medium for growing acid producing bacteria comprising in admixture: a powdered or aqueous bacterial growth medium including a carbohydrate source and a nitrogen source assimilatable by the bacteria, wherein the powder can be dissolved or dispersed in water to provide the aqueous growth medium with an initial pH between about 4 and 8.5; and an essentially water insoluble or temporarily water insolubilized and thus initially solid form of a non-toxic neutralizing agent which is a base, basic salt or mixture thereof, wherein a portion of the insoluble or the insolubilized neutralizing agent remains in solid form in the aqueous medium over a period of time and wherein the neutralizing agent maintains a pH in the aqueous medium at a level which provides for growth of the bacteria by a controlled reaction of the neutralizing agent with at least a part of the acid produced by the bacteria over the period of time they are grown.

The present invention further relates to a bacterial composition which comprises in admixture: acid producing bacteria which have been grown in an aqueous growth medium including an assimilatable carbohydrate source and a nitrogen source to a concentration of at least about $10^5$ cells per ml; and an essentially water insoluble or temporarily water insolubilized and thus initially solid form of a neutralizing agent which is a base, basic salt or mixture thereof such that when acid is produced by the bacteria at least a part is neutralized.

The term "controlled reaction" as used herein includes the use of a neutralizing agent: (1) which is essentially water insoluble and thus substantially insoluble in a neutral growth medium and which reacts with acid as it is produced by the bacteria; or, (2) which is temporarily water insoluble because it is coated with or compounded with a binder or coating which dissolves or disperses or becomes porous in the medium to release the neutralizing agent as a function of time which then allows the agent to react with the acid. This latter type of controlled reaction is referred to herein as a "controlled release". In both instances the pH of the growth medium is maintained by the solid form of the neutralizing agent at a level which promotes growth of the bacteria over a period of time.

The phrase "neutralizing agent" means any compound or composition which reacts with or binds with hydrogen ions to maintain or raise the pH of an aqueous solution. The phrase "essentially water insoluble" means a neutralizing agent which has a solubility in water (having a neutral pH without the agent) at 25° C. of less than about 10 grams/liter. Based upon the definitions in the United States Pharmacopoeia XIX(1975) compounds are "slightly soluble" at 1.0 gm to 10.0 gm per liter; "very slightly soluble" at 0.1 gm per liter to 1.0 gm per liter and "practically insoluble", or "insoluble" at less than 0.1 gm per liter and the phrase "essentially water insoluble" covers all these solubilities.

The term "controlled release" as used herein includes, but is not limited to, the terms such as delayed release, extended release, pH-dependent release, prolonged release, sustained release and repeat release and includes slowly dissolving or slowly available solid forms of the neutralizing agent which may be powder, granules or tablets and which may or may not have been encapsulated or in any other way formulated to produce the desired release of the neutralizing agent.

Neutralizing agents or chemicals which control the pH by reacting with the acid include, but are not limited to, non-toxic, mono-, di-, and tri-valent cations, such as metals, ammonium, and organic groups associated with anionic groups including for instance, hydroxides and basic salts of phosphates, carbonates, and citrates. In particular, preferred neutralizing agents as bases or salts include, sodium carbonate, sodium bicarbonate, ammonium bicarbonate, potassium bicarbonate, magnesium oxide, dibasic ammonium phosphate, monobasic ammonium phosphate, dibasic sodium phosphate, monobasic sodium phosphate, magnesium phosphate tribasic, magnesium phosphate dibasic, magnesium orthophosphate, magnesium orthophosphate mono-hydrogen, magnesium pyrophosphate, calcium phosphate tribasic, calcium phosphate dibasic, calcium phosphate monobasic, calcium carbonate, ammonium carbonate, magnesium carbonate and/or magnesium hydroxide, magnesium ammonium phosphate; zinc oxide; calcium oxide, potassium carbonate, sodium hydroxide and potassium hydroxide; liquid or gaseous bases such as ammonium hydroxide or ammonia which may be absorbed or adsorbed in another material and anion exchange resins, or cation exchange resins such as the polystyrene-divinylbenzene resins including: Chelex 100 ® (cation), Dowex ® 50WX 4 (cation) from Bio-Rad Laboratories, Richland, Calif.; the salts of a carboxylic acid on an acrylic polymer lattice such as Bio-Rex TM 70 (cation) from Bio-Rad; the methacrylic acid divinylbenzene resins such as Amberlite ® DP-1 (cation); and IRC ® 50 (cation) from Rohm and Haas; and the polyalkyleneamine lattice resins such as Bio-Rex TM 5 (anion) from Bio-Rad. The ion exchange resins are in a form which removes the acid ions from solutions. The cation exchange resins are always in the salt form in order to neutralize hydrogen ions. The inorganic neutralizing agents are preferred since they are generally non-toxic to the bacteria; however, organic neutralizing agents such as the exchange resins and water soluble trisodium citrate, disodium citrate, triammonium citrate, ammonium citrate dibasic and sodium glycerophosphate can be used. Generally the alkali metal and alkaline earth metal bases or salts are preferred as the acid neutralizing agents.

The neutralizing agents are preferably insolubilized by being: (1) encapsulated with a coating of a material which provides a controlled release of the neutralizing agent to the growth medium over a period of time; or, (2) mixed as a powder with a binder which provides a controlled release of the neutralizing agent to the medium. Binding and coating agents used to provide the controlled released include materials such as cellulose ethers (ethyl cellulose, methylcellulose and their derivatives such as hydroxypropyl, hydroxybutyl, and the like) and other modified celluloses, carnauba wax; carbopol; starch; acacia; sodium caseinate; nylon, glycerol tristearate; beeswax; and other high molecular weight fats, waxes and polymer materials and other organic materials, which can be used to bind or coat or in any other way affect the controlled release of the neutralizing agents. The neutralizing agents can be in the form of: (1) particles of about the same size which are provided with coatings of varying thicknesses, or, (2) particles of varying size which slowly release the neutralizing agent to the medium upon the dissolution of the coatings of essentially the same thickness.

The solid form of the essentially insoluble or the insolubilized neutralizing agent can be added to various culture media used to grow acid-producing bacteria which are then used as bacterial starters for making fermented animal and human food and beverage products. As a result of the invention, the neutralizing agent is gradually available during the growth period such that the pH of the medium is prevented from changing as rapidly or as completely and, as a result, a higher number of cells are produced and the cells are more stable and active in fermentations because they have not been injured by the acids. The solid neutralizing agent can also be used directly in the food or beverage product so long as it is substantially neutralized upon the completion of the fermentation.

The present invention also includes the use of essentially water insoluble acid neutralizing agents without any coatings or binders in a powder, granule, tablet or pellet form which slowly react in the growth medium with acid as it is generated by the bacteria. Included in this group of agents are most of the alkaline earth metal salts and bases which are essentially water insoluble. These neutralizing agents thus do not dissolve significantly in a substantially neutral growth medium.

The solid form of the neutralizing agent is available in the growth medium over a period of time without substantially increasing the pH of the medium. Generally the neutralizing agent with the acid maintains a pH in the range of between about 5 and 7. Thus the acid is at least partially neutralized during growth. The acidity is controlled until there is no longer a need such as when growth or acid production by the bacteria is completed. Care should be taken to make certain that the bacteria are not impaired or killed by their own acidity if they are to be used subsequently in a fermentation process.

Generally the acid producing bacteria are lactic acid, propionic and/or acetic acid producing and are used for edible products for animals and humans. Included as foods are fermented animal feeds, dairy products, meats, vegetables, beverages, such as fermented milks, and the like. Other organic acids are produced by bacteria and these are neutralized in the same manner.

The nutrients used in growth media are well known and include an assimilatable carbohydrate and nitrogen or amino acid source and usually essential minerals where the object is to increase the number of bacteria. The carbohydrates are usually in the form of simple sugars such as lactose or glucose which are directly metabolized by the bacteria to produce the acids. The nitrogen sources preferably include various forms of yeast such as yeast extract or other sources of assimilatable amino acids such as tryptone, casein, phytone, peptone, and beef extract. The essential minerals vary from bacteria to bacteria but generally include trace amounts of transition metal salts such as manganese and magnesium salts. Many variations in growth media are described in the prior art and will be obvious to one skilled in the art.

The bulk starters include the insoluble or insolubilized solid neutralizing agent in a powdered or aqueous growth media with the growth materials. The media generally have a pH in water of between about 4 and 8.5. The solid neutralizing agent maintains a pH in the medium of above about 5 during growth of the bacteria.

The bacterial compositions can be used directly for fermentation or stored for a period of time. They can be concentrated, particularly mechanically as by centrifuging, and frozen or lyophilized for storage using various conventional stabilizing agents. All of these variations are well known to those skilled in the art.

It has been found that by incorporating between about 0.1 and 10 parts by weight of the insoluble or insolubilized, solid neutralizing agent per 100 parts of the growth medium by weight containing at least about $1 \times 10^5$ cells per ml that the compositions are more stable upon storage. Preferably the bacteria are grown to a concentration above about $1 \times 10^8$ cells per ml, or even $1 \times 10^9$ cells per ml, and then mechanically concentrated from above $1 \times 10^9$ cells per ml up to about $1 \times 10^{15}$ cells per ml. It is contemplated that the cells could be grown in a conventional manner, preferably using liquid or gaseous neutralizing agents periodically added to the medium, and then the insoluble or insolublized neutralizing agent added to provide stability upon use or storage. Between about 0.1 and 10 parts by weight of the insoluble or insolubilized neutralizing agent are added per 100 parts by weight of the concentrated cells.

SPECIFIC DESCRIPTION

Examples of the present invention are set forth hereinafter. It is intended that they be only illustrative. The depository for the cultures is Oregon State University in Corvallis, Oreg. and the cultures are freely available without cost to the public.

EXAMPLE 1

Sodium carbonate as the neutralizing agent was mixed with one percent magnesium stearate as a lubricant and compressed into tablets. Any commercial tablet making machine will work and in this example a model TPK-12 TM tablet making machine made by Chemical and Pharmaceutical Industry Company was used. The tablets were spray coated in a rotating coating pan with a mixture of by weight 50% methyl cellulose (Methocel ® E15) and 50% ethyl cellulose (Ethocel ® 45) with a 1%, 2%, 3%, 4%, 5% and 6% coating by weight. The thickness of the coating is dependent on the tablet size and these tablets weighed about 0.310 g. Other tablet sizes and various amounts of coating mixtures were used successfully.

A growth medium was prepared by suspending 86 g of Actilac ® a conventional bacterial growth medium including dried whey, nonfat dry milk, sodium citrate and dried autolyzed yeast, in 700 ml of water with stirring at 50 rpm and heating to 80° C. Thirty-two (32) tablets containing sodium carbonate with a 5% coating of the cellulose ethers were added and the mixture was maintained at 80° C. for 45 minutes. A control growth medium was prepared in an identical manner without the sodium carbonate tablets.

After cooling to 27° C., the medium was inoculated with *Streptococcus cremoris* 108 at a level of $10^4$ to $10^6$ cells per ml and the pH was monitored in comparison to the control medium without added tablets. The release of the sodium carbonate to the medium is controlled to a certain extent by adjusting media agitation or stirring. The pH immediately after inoculation was 6.29 for the control and 6.41 for the invention; after 14.5 hours, the pH was 4.81 for the control and 5.20 for the invention. In a second determination, the medium containing tablets with a 6% coating had an initial pH of 6.36 compared to 6.32 for the control and a pH after 19 hr. of 5.32 compared to 4.76 for the control. This shows a considerable control of the pH, using a temporarily insolubilized neutralizing salt.

Activity testing by growth in nonfat milk medium for 6 hours at 30° C. using a 1% by volume bacterial inoculum in a 11% by weight nonfat milk medium showed the bacterial composition prepared by addition of sodium carbonate tablets with the 6% coating had the maximum possible activity for the bacteria as determined by comparison to a culture grown conventionally by a continuous addition of ammonium hydroxide for pH maintenance at pH 6.0.

EXAMPLE 2

One kg of anhydrous granular sodium hydrogen phosphate dibasic was mixed with 50 g of ethyl cellulose (Ethocel ® 45) of Example 1. To this mixture, 300 ml of a 70/30 percent by volume mixture of methylene chloride and ethanol 95% was added and mixed for 5 minutes. The mixture was pressed through a number 6 screen to produce granules. The granules were dried, tableted and coated with a 6% coating of methyl cellulose and ethyl cellulose (Methocel ® E15/Ethocel ® 45) 70%/30% by weight.

The tablets were placed in the growth medium of Example 1. After the addition, the medium was agitated at 64 rpm and maintained at 80° C. for 45 minutes. Thereafter, the medium was cooled to 27° C. and innoculated with Streptococcus cremoris 108, as in Example 1. The initial pH values were 7.11 for the invention and 6.43 for the control. After 12.25 hours the pH was 6.68 for the invention and 4.92 for the control and after 33.25 hours the invention pH was 5.62 and the control pH was 4.93. In a separate test where the medium containing the tablets was not stirred until about 4.75 hours post inoculation, the initial invention pH was 6.44 and 6.35 for the control and after 16 hours was 5.29 for the invention and 4.81 for the control. In each of the above examples the activity of the bacteria was greater for the media containing the temporarily insolubilized neutralizing salt than for the control.

EXAMPLE 3

A growth medium was prepared consisting of a mixture of the following ingredients by weight: 3.5% sweet whey powder; 0.5% yeast extract; 0.5% potassium phosphate dibasic; 0.25% potassium phosphate monobasic. After dissolving the mixture in water, it was autoclaved at 121° C. for 10 minutes and then rapidly cooled. To the cooled mixture was added 5 gm of temporarily insolubilized particles which had been prepared by mixing 10 g of carboxypolymethylene (Carbopol 941$_{t.m.}$) with 300 gm of ammonium hydrogen phosphate dibasic and with 50 ml of water, spreading the mixture out to dry at 45° C. overnight and breaking the mixture into pieces.

A 1% by volume inoculum of a Streptococcus lactis frozen culture (Fargo ® mixed strain starter culture No. 1105) commercially available from Microlife Technics, Inc., Sarasota, Fla. containing about $10^9$ cells per ml, was then added to the medium with the insolubilized particles. The fermentation mixture was incubated at 30° C. with gentle agitation over a 12 hour period. The pH of the fermentation was continuously recorded by a strip chart recorder. A second fermentation was performed in exactly the same manner, except the insolubilized ammonium phosphate was omitted from the growth medium.

The initial pH of the media was 6.7; after 8 hours the medium of the invention was pH 6.6 and was 5.1 for the control and after 12 hours the pH for the invention was 5.1 and was 4.7 for the control.

During a 10 day storage period of the bacteria at 5° C., measurements of activity in nonfat dry milk were conducted. The medium of the invention produced cells with activity which were superior to the cells produced in medium without the controlled release as shown by Table I.

TABLE I

| Storage Time (hrs.) | Activity[a] Controlled Release Base | Control |
|---|---|---|
| 0 | 5.30 | 5.36 |
| 8 | 5.25 | 5.48 |
| 96 | 5.28 | 5.94 |
| 240 | 5.36 | 6.33 |

[a]Final pH after incubation at 30° C. for 6 hr. of a 1% by volume inoculum in a 11% by weight solids nonfat milk medium.

EXAMPLE 4

A growth medium was prepared from the following ingredients: 3.5% sweet whey powder; 0.5% yeast extract; 0.5% sodium beta-glycerophosphate; 0.83% sodium citrate; 0.17% ammonium citrate dibasic. After the mixture was dissolved in water, it was heated with high agitation to a temperature of 85°–90° C. and held there for 45 minutes. The heat-treated medium was then rapidly cooled in an ice bath. The controlled release ingredient consisted of 10 g of a 50/50 by weight mixture of sodium carbonate tablets coated with 1% or 1.25% by weight of ethyl cellulose (Ethocel ® 45). The coating was applied by spraying a solution of ethyl cellulose dissolved in methylene chloride onto tumbling tablets in a standard tablet coating pan.

The medium was then inoculated with Streptococcus lactis B1 (Oregon State University) (1% by volume containing $10^8$ cells per ml) and incubated at 27° C. with gentle agitation over a 16 hour period to provide the release of the neutralizing agent. A record of the fermentation pH was made using a strip chart recorder.

A second fermentation was done exactly in the same manner except the controlled release component had a 10% by weight ethyl cellulose coating which prevented adequate release of the sodium carbonate and the pH was not maintained above 5.0.

Following the 16 hour fermentation, a portion of the fermentation mixture was stored at 21° C. for a period of 10 days during which measurements of starter cell activity and cell numbers were periodically made. The controlled release medium which maintained the pH above 5.5 throughout the 16 hour period resulted in starter cells that had greater activity and higher numbers compared to the fermentation where the pH went below 5.0 where acid injury was evident. The data is presented below for both the pH during the fermentation in Table II and activity during storage in Table III.

TABLE II

| Fermentation Time (Hours) | Controlled Release | Control |
|---|---|---|
| 0 | 6.7 | 6.3 |
| 2 | 6.9 | 6.4 |
| 4 | 6.8 | 6.5 |
| 6 | 6.2 | 6.5 |
| 8 | 5.9 | 6.0 |
| 10 | 5.7 | 5.1 |

TABLE II-continued

| Fermentation Time (Hours) | Controlled Release | Control |
|---|---|---|
| 12 | 5.6 | 4.8 |
| 16 | 5.6 | 4.7 |

TABLE III

| Storage Time (Days) | Controlled Release Activity (pH) 6 hr - 30° C. | SCC[a] | cfu/ml[b] | Control Activity (pH) 6 hr - 30° C. | SCC[a] | cfu/ml[b] |
|---|---|---|---|---|---|---|
| 0 | 4.76 | 4.93 | $8.1 \times 10^9$ | 4.75 | 4.95 | $1.4 \times 10^{10}$ |
| 1 | 4.79 | 4.96 | $8.8 \times 10^9$ | 4.84 | — | $1.4 \times 10^{10}$ |
| 2 | 4.81 | 4.95 | $8.2 \times 10^9$ | 5.08 | — | $1.1 \times 10^{10}$ |
| 4 | 4.86 | 4.99 | $7.8 \times 10^9$ | 5.97 | 6.08 | $5.6 \times 10^9$ |
| 7 | 5.26 | 5.39 | $7.7 \times 10^9$ | — | — | — |
| 10 | 5.62 | — | $6.7 \times 10^9$ | 6.29 | 6.28 | $2.0 \times 10^6$ |

[a]SCC = simulated Cheddar cheese activity test described in the New Zealand Journal of Dairy Technology 4:246, 1969 which is a measurement of the pH attained by culture acid production during simulated Cheddar cheese production.
[b]cfu/ml = viable colony forming units or cells per ml.

The cells were more viable due to the controlled release of the method of the present invention as can be seen from Table III.

EXAMPLE 5

A growth medium was prepared in the same manner as set forth in Example 4. Ten grams (10 g) of pan-coated sodium carbonate granules coated with ethyl cellulose (20% Ethocel ® 45) were added to the medium which was then inoculated with 1% by volume *Streptococcus lactis* B1 (Oregon State University) containing $10^8$ cells per ml and the same fermentation conditions were applied as described in Example 4. A second fermentation was performed in the same manner except the controlled release granules were omitted. A third fermentation was done exactly like the other two except uncoated sodium carbonate was added in place of the granules.

As in Example 4, the cells from completed fermentation of Table IV were stored at 21° C. for 10 days, during which the activity and cell numbers were determined. The results are tabulated below in Tables IV, V, VI and VIA. The third fermentation (control b) produced no significant results and impaired or killed large numbers of bacteria.

TABLE IV

| Fermentation Time (Hours) | Observed pH Controlled Release Alkali | Control[a] | Control[b] |
|---|---|---|---|
| 0 | 6.4 | 6.5 | 10.1 |
| 2 | 6.7 | 6.5 | — |
| 4 | 7.0 | 6.4 | — |
| 6 | 6.6 | 5.9 | — |
| 8 | 5.7 | 4.9 | — |
| 10 | 5.0 | 4.7 | — |
| 12 | 5.0 | 4.7 | — |
| 16 | 5.0 | 4.7 | 10.1 |

[a]without alkali
[b]alkali without controlled release

TABLE V

| | Activity and Cell Population Data | | |
|---|---|---|---|
| | Controlled Release Activity | Control[a] | Control[b] |
| 6 hr at 30° C. activity (pH) | 4.92 | 5.11 | 6.55 |
| cfu/ml | $9.2 \times 10^9$ | $3.3 \times 10^9$ | $3.1 \times 10^6$ |

TABLE VI

| Storage Time (days) | Controlled Release Activity (6 hr - 30° C. pH) | Cell Count cfu/ml |
|---|---|---|
| 0 | 4.92 | $9.2 \times 10^9$ |
| 2 | — | — |
| 4 | 5.17 | $7.0 \times 10^9$ |
| 7 | 5.23 | $5.6 \times 10^9$ |
| 10 | 5.39 | $5.4 \times 10^9$ |

TABLE VI-A*

| Storage Time (days) | Control Activity (6 hr - 30° C. pH) | Cell Count cfu/ml |
|---|---|---|
| 0 | 5.11 | $3.3 \times 10^9$ |
| 2 | 5.73 | $2.2 \times 10^9$ |
| 4 | 6.12 | $3.6 \times 10^8$ |
| 7 | 6.27 | $1.4 \times 10^8$ |
| 10 | 6.30 | $1.1 \times 10^7$ |

*Control "a" cultures

EXAMPLE 6

Sodium carbonate tablets (1 gram each) were pan-coated with ethyl cellulose (Ethocel ® 45) dissolved in methylene chloride/acetone (50/50 by volume) with a coating by weight varying around 1% (0.85–1.25%). The tablets (10 per 700 ml) were then added to the Actilac ® growth medium of Example 1 which was inoculated with *Streptococcus cremoris* 134 (Oregon State University) at $10^8$ cells per ml. The pH was monitored in comparison to control medium without added tablets. The pH data after 16 hours at 27° C. were as shown in Table VII.

TABLE VII

| % Coating | pH |
|---|---|
| —* | 4.9 |
| .85 | 5.5 |
| .95 | 5.5 |
| 1.05 | 5.1 |
| 1.15 | 5.4 |
| 1.25 | 5.2 |

*no added tablets - Actilac ® control

Tablets coated with 0.85% ethyl cellulose were used in a second fermentation in order to determine the number and activity of cells generated. After 16 hours at 27° C., the control Actilac ® culture had a pH of 4.5 while the tablet-coating culture had a pH of 5.0. The control and controlled release cultures were stored at about 25° C. (ambient temperatures) and tested for acid-producing activity (pH achieved from 1% by volume inoculation into 11% by weight nonfat milk incubated 6 hours at 30° C.) and cell numbers. During the 10 day storage period, the pH of the controlled release culture was adjusted to pH 5.0 with sterile 5 N sodium carbonate at daily intervals. The results were as shown in Table VIII.

TABLE VIII

| Days | Control pH | Control cfu/ml | Controlled Release pH | Controlled Release cfu/ml |
|---|---|---|---|---|
| 0 | 5.0 | $2.2 \times 10^8$ | 4.8 | $2.7 \times 10^8$ |
| 2 | 5.9 | $1.4 \times 10^8$ | 5.4 | $2.2 \times 10^8$ |
| 4 | 6.4 | $1.3 \times 10^6$ | 5.5 | $2.2 \times 10^8$ |
| 8 | —* | — | 6.1 | $2.5 \times 10^8$ |
| 10 | —* | — | 6.2 | $3.1 \times 10^8$ |

*cells inactive

These data show that the cell population produced with the neutralizing agent tablets was stable for 10 days and that activity was extended significantly beyond the control since they were not impaired by the lower pH.

EXAMPLE 7

A growth medium was prepared by mixing 21 g of whey powder with 3.5 g of yeast extract, 1.0 g of citric acid and 20 g of magnesium phosphate tribasic which is an essentially water insoluble neutralizing agent. This mixture was suspended in 700 ml of water, heated to 85° C. for 45 minutes, cooled to 27° C. and inoculated with a lactic acid-producing microorganism which was *Streptococcus lactis* 134 (Oregon State University) at $10^8$ cells per ml. A control medium without the citric acid and the magnesium phosphate tribasic was treated in a similar manner. Another medium containing 21 g of whey powder with 3.5 g of yeast, 2 g of citric acid and 10 g of calcium carbonate which is also an essentially water insoluble neutralizing agent was treated similarly. The pH values of the growth media after inoculation are shown in Table IX. The citric acid was used to initially adjust the pH.

TABLE IX

| Time (Hours) | pH-Treatment 1 (magnesium phosphate tribasic) | pH-Treatment 2 Calcium carbonate | pH-control |
|---|---|---|---|
| 0 | 7.00 | 6.52 | 6.03 |
| 2.25 | 7.01 | 6.63 | 6.08 |
| 3.33 | 7.07 | 6.67 | 6.16 |
| 4.33 | 7.03 | 6.69 | 6.06 |
| 8.33 | 6.78 | 6.22 | 5.72 |
| 9.00 | 6.65 | 6.15 | 5.58 |
| 9.50 | 6.59 | 6.06 | 5.48 |
| 10.00 | 6.50 | 5.97 | 5.41 |

The starter culture for the products containing calcium carbonate or magnesium phosphate had increased activity relative to the control. Similar fermentations using 2, 3 or 4 times as much calcium carbonate or magnesium phosphate gave very similar results.

Other fermentations repeating Examples 1 to 7 using anion/cation exchange resins as well as different amounts of sodium phosphate monobasic, ammonium phosphate monobasic, ammonium citrate dibasic or disodium citrate as the insoluble or insolubilized neutralizing agents were performed and the acid produced was at least partially neutralized and the activity of the resultant bacteria was higher than from the control fermentations.

COMPARATIVE EXAMPLE 8

Actilac ® growth medium was placed in 700 ml of water to achieve a solids level of 11% by weight, heated to 85°-90° C. for 45 minutes, cooled to 27° C. and inoculated with a one percent (1%) by volume with a lactic streptococcal (*Streptococcus cremoris* 134 (Oregon State University) $10^8$ cells per ml) starter culture. Fermentation was continued for 12 hours at 27° C., when a pH of 4.6 was achieved, and then sterile 5 N sodium carbonate was added to raise the pH to 7.0. The fermentation was allowed to continue for an additional 4 hours (pH was 5.4) for a total fermentation time of 16 hours. Samples were taken at 8 hours and at 16 hours, stored at 25° C. and at 5° C. and analyzed daily for stability as determined by acid-producing activity and number of viable bacteria present per milliliter. These data, shown in Tables X and XI below, allowed activity comparison of controlled-release base produced cells with cells produced when alkali was added late in the fermentation.

TABLE X

Data on cells sampled at 8 hours

| Storage Time (Days) | Activity (pH) 6 hr - 30° C. 5° C. | Activity (pH) 6 hr - 30° C. 25° C. | SCC 5° C. | SCC 25° C. | cfu/ml 5° C. | cfu/ml 25° C. |
|---|---|---|---|---|---|---|
| 0 | 4.88 | 4.88 | 5.10 | 5.10 | $2.1 \times 10^8$ | $2.1 \times 10^8$ |
| 1 | 5.65 | 5.62 | 5.99 | 6.03 | $5.4 \times 10^7$ | $1.5 \times 10^8$ |
| 2 | 5.83 | 6.24 | 6.09 | 6.31 | $3.5 \times 10^7$ | $2.2 \times 10^7$ |
| 4 | 5.96 | 6.37 | — | — | $3.9 \times 10^7$ | $1.8 \times 10^6$ |
| 7 | 6.09 | 6.37 | — | — | $4.9 \times 10^7$ | $<4.0 \times 10^4$ |

TABLE XI

Data on cells sampled at 16 hours

| Storage Time (Days) | Activity (pH) 6 hr - 30° C. 5° C. | Activity (pH) 6 hr - 30° C. 25° C. | SCC 5° C. | SCC 25° C. | cfu/ml 5° C. | cfu/ml 25° C. |
|---|---|---|---|---|---|---|
| 0 | 4.74 | 4.74 | 4.90 | 4.90 | $4.9 \times 10^8$ | $5.6 \times 10^8$ |
| 1 | 5.03 | 4.90 | 5.49 | 5.22 | $2.8 \times 10^8$ | $6.4 \times 10^8$ |
| 2 | 5.95 | 5.12 | 6.18 | 5.46 | $9.1 \times 10^7$ | $5.0 \times 10^8$ |
| 4 | 6.26 | 6.22 | — | — | $1.9 \times 10^7$ | $1.3 \times 10^8$ |
| 7 | 6.30 | 6.38 | — | — | $1.3 \times 10^7$ | $1.6 \times 10^6$ |

Comparison of these data to those generated for Example 4 illustrate the advantages of the timed-release pH control methods over that of adding alkali late in the fermentation to neutralize acid present. The cells are acid damaged.

EXAMPLE 9

Starter culture was prepared in a medium containing 3.5% whey powder, 0.5% yeast extract, 3.6% magnesium phosphate tribasic, 0.5% dibasic ammonium citrate and 0.5% tribasic sodium citrate dihydrate as in the first treatment of Example 7 and a control culture was prepared by inoculation of 11% solids nonfat milk followed by incubation at 27° C. also for 16 hrs to a pH of 4.4 which damaged the cells due to acidity. The two cultures were compared for acid-producing activity, viable cell counts and for acid production during the manufacture of Cheddar cheese using acceptable industry procedures but with only a 0.5% by volume ($5 \times 10^7$ cells per ml) inoculum as compared to the 1 to 3% by volume customarily used. For the culture produced under the influence of the water insoluble or insolubilized neutralizing agent, the pH value by the 6 hour 30° C. activity test was 4.75 and for the SCC test it was 4.89 and the viable cell count was $1.1 \times 10^9$ cfu per milliliter. For the control culture these pH values were 4.94 and 5.30, respectively and the viable cell count was $1.6 \times 10^9$. The culture produced with pH-dependent released neutralizing agent was noticeably more active during cheese making as shown by the data in Table XII.

TABLE XII

| Step | Titratable Acidity | |
|---|---|---|
| | Test Culture* | Nonfat Milk Culture |
| Raw Milk | 0.15 | 0.15 |
| After 30 minute ripening | 0.15 | 0.15 |
| After cutting | 0.10 | 0.10 |
| After washing | 0.12 | 0.10 |
| Start cheddaring | 0.24 | 0.18 |
| Half cheddared | 0.37 | 0.20 |
| End of cheddaring | 0.47 | 0.30 |

*pH controlled culture prepared as in the first treatment of Example 7. These data show the superior acid-producing activity of the bacterial starter cultures produced by the present invention.

EXAMPLE 10

Another medium formulation containing magnesium phosphate tribasic was evaluated for growth, pH maintenance and phage inhibition. The medium contained by weight 1.5% magnesium phosphate tribasic, 1.5% ammonium phosphate dibasic, 1.5% tribasic sodium citrate dihyrate, 3.5% sweet whey powder and 0.5% yeast estract. It was heat treated as in Example 7. Evaluation was made in comparison to nonfat dry milk (11% solids), a leading phage inhibitory medium (HL-100; Chr. Hansen's Laboratory, Inc., Milwaukee, Wis.) and the continuous whey neutralization process now practiced in industry and described by Richardson (*Dairy and Ice Cream Field* 161(9): 80A–80D (1978)). Fermentation was at 21° C. The continuous neutralization process uses 27° C. in industry, however this is not a significant difference. One percent inoculum was made with *Streptococcus cremoris* 205 (Oregon State University) and the homologous phage T189 ($10^5$ phages per ml) was used to evaluate the phage inhibition. Table XIII below shows the superior growth promoting, phage inhibitory and active cell generating properties of the medium containing magnesium phosphate as the water insoluble neutralizing agent. Also shown in Table XIII are data indicating that the cells produced by the controlled release of the neutralizing agent are not in an injured state and therefore maintain acid producing activity for at least 24 hours at ambient room temperature.

TABLE XIII

| | Acid Producing Activity$^a$ | | | | Cell Numbers (cfu/ml) | | Phage Inhibition | |
|---|---|---|---|---|---|---|---|---|
| | 0hr | | 24 hr$^b$ | | | | | |
| | Δ4 | Δ6 | Δ4 | Δ6 | 0hr | 24 hr | Phage added/ml | Phage recovered |
| NDM (11% W/W) | 0.44 | 1.05 | 0.34 | 0.69 | $2.0 \times 10^9$ | $2.0 \times 10^9$ | $9.2 \times 10^4$ | $4.2 \times 10^9$ |
| HL 100 (11.5% W/W) | 0.69 | 1.42 | 0.46 | 1.05 | $2.9 \times 10^9$ | $2.8 \times 10^9$ | $8.7 \times 10^4$ | $2.5 \times 10^5$ |
| Continuous Neutralization | 0.99 | 1.60 | 0.72 | 1.41 | $7.2 \times 10^9$ | $9.2 \times 10^9$ | $9.2 \times 10^4$ | $6.4 \times 10^7$ |
| 1.5/1.5/1.5 Medium | 1.14 | 1.69 | 0.75 | 1.44 | $1.0 \times 10^{10}$ | $8.5 \times 10^9$ | $8.7 \times 10^4$ | $2.3 \times 10^3$ |

$^a$6 hr - 30° C. activity test with pH readings at 4 hr and 6 hr (Δ4 and Δ6 are changes in pH after 4 and 6 hrs, respectively).
$^b$activity after storage for 24 hours at room temperature The magnesium phosphate-containing medium was also evaluated for inhibition of other lactic streptococcal bacteriophage. Data showing that the controlled release medium prevents phage replication and causes a reduction in phage titer appear in Table XIV.

TABLE XIV

| Phage/Host | ∅ added/ml | ∅ recovered/ml |
|---|---|---|
| T189/205 | $8.7 \times 10^4$ | $2.3 \times 10^3$ |
| Ml₈/ML₈* | $3.1 \times 10^4$ | $4.3 \times 10^3$ |
| hp/HP | $4.4 \times 10^4$ | $<1.0 \times 10^3$ |
| h₂/H2 | $3.7 \times 10^4$ | $<1.0 \times 10^3$ |

TABLE XIV-continued

| Phage/Host | ∅ added/ml | ∅ recovered/ml |
|---|---|---|
| C2/C2* | $5.9 \times 10^4$ | $<1.0 \times 10^3$ |

*Streptococcus lactis* strains; other strains are *Streptococcus cremoris* "∅" means phage and all are available at Oregon State University.

The specific improvements of the present invention thus include: (1) the use of the essentially water insoluble or temporarily insolubilized acid neutralizing agents which may be incorporated initially or added at any time to fermentation systems such that the agent is available at a rate to at least partially neutralize acid produced during the growth or fermentation process. (2) The use of a mixture of bulk starters including essential growth chemicals with powdered, pelleted, tableted or granulated essentially insoluble or insolubilized neutralizing agents, with sufficient amounts of acidic materials to obtain the desired initial pH for use as culture media for bacterial starter production for use in the preparation of cheese and for other food or even nonfood products prepared by fermentation. (3) The use of the essentially water insoluble or temporarily water insolubilized neutralizing agents in the dry form or after dissolution in bacterial cultures.

We claim:

1. In a method for growing acid producing bacteria to be used in fermenting foods by inoculating the bacteria into a growth medium containing water and nutrients for the bacteria, growing the bacteria in the growth medium, and using the bacteria so grown for fermenting the food the improvement which comprises:

(a) providing a temporarily water insolubilized and thus initially solid form of a nontoxic, ordinarily water soluble neutralizing agent which is a base, basic salt or mixture thereof in intimate contact with the growth medium, the neutralizing agent being insolubilized in such a form that the neutralizing agent is gradually released from the solid form into the medium over a period of time, and wherein the growth medium and neutralizing agent, in combination, are adapted for growing acid producing bacteria to be used in fermenting the food;

(b) growing the bacteria in the growth medium in the presence of the insolubilized neutralizing agent, wherein a pH range in the medium is maintained above about 5 for so long as desired to promote growth of the bacteria by a controlled reaction of the released neutralizing agent with at least a part of the acid produced by the bacteria in the medium over the period of time; and (c) fermenting the food with the bacteria after they have been grown in the growth medium including the neutralizing agent.

2. In a method for growing acid producing bacteria by inoculating the bacteria into a growth medium containing water and nutrients for the bacteria and then growing the bacteria in the growth medium the improvement which comprises:
   (a) providing a temporarily water insolubilized and thus initially solid form of a nontoxic, ordinarily water soluble neutralizing agent which is an alkali metal or alkaline earth metal base or basic salt or mixture thereof in the growth medium, the agent being provided by coating particles of the agent with a material which provides a controlled release of the agent over a period of time; and
   (b) growing the bacteria in the growth medium in the presence of the insolubilized neutralizing agent, wherein a pH range in the medium is maintained so as to promote growth of the bacteria by a controlled reaction of the insolubilized neutralizing agent with at least a part of the acid produced by the bacteria in the medium over the period of time.

3. In a method for growing acid producing bacteria by inoculating the bacteria into a growth medium containing water and nutrients for the bacteria and then growing the bacteria in the growth medium the improvement which comprises:
   (a) providing a temporarily water insolubilized and thus initially solid form of a nontoxic, ordinarily water soluble neutralizing agent which is an alkali metal or alkaline earth metal base or basic salt or mixture thereof in the growth medium, the agent being insolubilized by compressing the agent as a powder in admixture with a binder to provide particle that release the agent into the growth medium over a period of time; and
   (b) growing the bacteria in the growth medium in the presence of the insolubilized neutralizing agent, wherein a pH range in the medium is maintained so as to promote growth of the bacteria by a controlled reaction of the insolubilized neutralizing agent with at least a part of the acid produced by the bacteria in the medium over the period of time.

4. The method of claim 1 wherein in addition after growing the bacteria are stored.

5. The method of claim 1 wherein in addition after growing the bacteria are mechanically concentrated to remove some of the aqueous growth medium and then frozen for storage.

6. The method of claim 1 wherein in addition after growing the bacteria are lyophilized for storage.

7. A bulk starter medium for growing acid producing bacteria for use in a food fermentation comprising in intimate admixture:
   (a) a powdered or aqueous bacteria growth medium including a carbohydrate source and a nitrogen source assimilable by the bacteria wherein the powder can be dissolved or dispersed in water to provide the aqueous growth medium with an initial pH between about 4 and 8.5; and
   (b) a temporarily water insolubilized and thus initially solid form of a nontoxic, ordinarily water soluble neutralizing agent which is a base, basic salt or mixture thereof, wherein a portion of the insoluble or the insolubilized neutralizing agent remains in solid form in the aqueous medium over a period of time and wherein the neutralizing agent maintains a pH in the aqueous medium above about 5 for so long as desired to enhance growth of the bacteria by a controlled reaction of the neutralizing agent with at least a part of the acid produced by the bacteria over the period of time they are grown, wherein the growth medium and neutralizing agent, in combination, are adapted for growing the acid producing bacteria for use in the food fermentation.

8. A bulk starter medium for growing acid producing bacteria comprising in admixture:
   (a) a powdered or aqueous bacterial growth medium including a carbohydrate source and a nitrogen source assimilable by the bacteria wherein the powder can be dissolved or dispersed in water to provide the aqueous growth medium with an initial pH between about 4 and 8.5; and
   (b) a temporarily water insolubilized and thus initially solid form of a nontoxic, ordinarily water soluble neutralizing agent which is an insolubilized particulate alkali metal or alkaline earth metal base or basic salt or mixture thereof, the agent having been insolubilized by being coated with a material which dissolves in the growth medium over a period of time to provide a controlled release of the base or salt into the growth medium at a rate which provides the pH of the medium above about 5 to provide for growth of the bacteria by a controlled reaction of the neutralizing agent with at least a part of the acid produced by the bacteria over the period of time they are grown.

9. The bulk starter of claim 8 wherein the coatings on the particles are of varying thicknesses and wherein the particles are of about the same size.

10. The bulk starter of claim 8 wherein the coatings on the particles are of essentially the same thicknesses, wherein the particles are of varying size, and wherein the particles release the neutralizing agent to the medium.

11. A bulk starter medium for growing acid producing bacteria comprising in admixture:
   (a) a powdered or aqueous bacterial growth medium including a carbohydrate source and a nitrogen source assimilable by the bacteria wherein the powder can be dissolved or dispersed in water to provide the aqueous growth medium with an initial pH between about 4 and 8.5; and
   (b) a temporarily water insolubilized and thus initially solid form of a nontoxic, ordinarily water soluble neutralizing agent which is an insolubilized particulate alkali metal or alkaline earth metal base or basic salt or mixture thereof, the agent having been insolubilized by being compressed as a powder in admixture with a binder to provide a controlled release of the agent into the growth medium to provide for growth of the bacteria by a controlled reaction of the neutralizing agent with at least a part of the acid produced by the bacteria over the period of time they are grown.

12. A bacterial composition for use in a food fermentation which comprises in intimate admixture:
   (a) acid producing bacteria which have been grown in an aqueous growth medium including an assimilable carbohydrate source and a nitrogen source to a concentration of at least about $10^5$ cells per ml; and
   (b) a temporarily water insolubilized and thus initially solid form of a nontoxic, ordinarily water soluble neutralizing agent which is a base, basic salt or mixture thereof such that when acid is produced by the bacteria at least a part is neutralized, wherein the growth medium and neutralizing agent, in combination, are maintained above about pH 5 for so long as desired to promote growth of the acid producing bacteria to be used in fermenting the food.

13. The bacterial composition of claim 12 wherein the cells have been grown in the presence of the neutralizing agent and the bacteria have been concentrated to a concentration of above about $10^9$ cells per ml by removal of some of the aqueous growth medium and have been admixed with the insolubilized solid neutralizing agent to provide the composition.

14. The bacterial composition of claim 12 wherein the bacteria have been grown to a concentration above about $10^9$ cells per ml and have been mixed with the insolubilized solid neutralizing agent.

15. The bacterial composition of claim 12 wherein the bacteria have been grown to a concentration above about $1 \times 10^8$ cells per ml with neutralization, wherein the bacteria are concentrated to above about $1 \times 10^9$ cells per ml to about $10^{15}$ cells per ml and then have been mixed with the insolubilized neutralizing agent.

16. The bacterial composition of claim 13, 14 or 15 wherein the bacteria are lactic acid producing.

17. The composition of claim 13, 14 or 15 wherein the composition is frozen for storage and shipment.

18. The composition of claim 13, 14 or 15 wherein the composition is lyophilized for storage and shipment.

* * * * *